(12) United States Patent
Spetz

(10) Patent No.: US 6,539,247 B2
(45) Date of Patent: *Mar. 25, 2003

(54) BRACHYTHERAPY SYSTEM FOR PROSTATE CANCER TREATMENT WITH COMPUTER IMPLEMENTED SYSTEMS AND PROCESSES TO FACILITATE PRE-IMPLANTATION PLANNING AND POST-IMPLANTATION EVALUATIONS WITH STORAGE OF MULTIPLE PLAN VARIATIONS FOR A SINGLE PATIENT

(75) Inventor: Kevin Stewart Spetz, Charlottesville, VA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/005,908

(22) Filed: Dec. 3, 2001

(65) Prior Publication Data

US 2002/0091315 A1 Jul. 11, 2002

Related U.S. Application Data

(60) Provisional application No. 60/076,226, filed on Feb. 27, 1998.

(51) Int. Cl.⁷ .................................................. A61B 5/05
(52) U.S. Cl. ............................................................... 600/427
(58) Field of Search ............................... 600/425, 426, 600/427, 428, 429, 462, 463, 464, 465, 466; 606/108, 130; 424/1.11, 1.33

(56) References Cited

U.S. PATENT DOCUMENTS

| | | |
|---|---|---|
| 3,783,251 A | 1/1974 | Pavkovich |
| 3,871,579 A | 3/1975 | Inamura |
| 3,987,281 A | 10/1976 | Hodes |
| 4,802,487 A | 2/1989 | Martin et al. |
| 4,911,170 A | 3/1990 | Thomas, III et al. |
| 4,917,097 A | 4/1990 | Proudian et al. |
| 4,958,639 A | 9/1990 | Uchiyama et al. |
| 5,027,818 A | 7/1991 | Bova et al. |
| 5,054,492 A | 10/1991 | Scribner et al. |
| 5,099,846 A | 3/1992 | Hardy |
| 5,107,839 A | 4/1992 | Houdek et al. |
| 5,117,829 A | 6/1992 | Miller et al. |
| 5,189,687 A | 2/1993 | Bova et al. |
| 5,205,289 A | 4/1993 | Hardy et al. |
| 5,261,404 A | 11/1993 | Mick et al. |
| 5,265,610 A | 11/1993 | Darrow et al. |
| 5,285,786 A | 2/1994 | Fujii |
| 5,297,037 A | 3/1994 | Ifuku |
| 5,303,148 A | 4/1994 | Mattson et al. |
| 5,305,748 A | 4/1994 | Wilk |

(List continued on next page.)

FOREIGN PATENT DOCUMENTS

| | | |
|---|---|---|
| JP | 10137238 A | 5/1998 |
| WO | WO 97/28743 | 8/1997 |

OTHER PUBLICATIONS

Hottier, F., A. Collet Billon, "3D Echography; Status and Perspective"; NATO ASI Series, vol. F60, 3D Imaging in Medicine, pp. 21–41, 1990.

(List continued on next page.)

*Primary Examiner*—George Manuel
(74) *Attorney, Agent, or Firm*—Bingham McCutchen LLP

(57) ABSTRACT

A system for assisting a user in preparing a brachytherapy pre-implantation plan and post-implantation evaluation for prostate cancer is disclosed. Image scans are loaded into the system. The user places seeds on the various image scans to treat the prostate cancer. The system of the present invention provides for creation of multiple variations to allow a user to compare and contrast plans or evaluations. A user can more easily move between variations of an original plan or evaluation, thereby simplifying the plan and evaluating process. Creation of multiple variations will depend upon altering certain user defined variables.

32 Claims, 5 Drawing Sheets

U.S. PATENT DOCUMENTS

| | | |
|---|---|---|
| 5,307,816 A | 5/1994 | Hashimoto et al. |
| 5,339,812 A | 8/1994 | Hardy et al. |
| 5,341,292 A | 8/1994 | Zamenhof |
| 5,345,938 A | 9/1994 | Nishiki et al. |
| 5,357,550 A | 10/1994 | Asahina et al. |
| 5,361,768 A | 11/1994 | Webler et al. |
| 5,373,844 A | 12/1994 | Smith et al. |
| 5,391,139 A | 2/1995 | Edmundson |
| 5,398,690 A | 3/1995 | Batten et al. |
| 5,409,000 A | 4/1995 | Imran |
| 5,418,715 A | 5/1995 | Deasy |
| 5,418,827 A | 5/1995 | Deasy et al. |
| 5,454,371 A | 10/1995 | Fenster |
| 5,458,125 A | 10/1995 | Schweikard |
| 5,485,839 A | 1/1996 | Aida et al. |
| 5,485,846 A | 1/1996 | Webler et al. |
| 5,497,776 A | 3/1996 | Yamazaki et al. |
| 5,511,549 A | 4/1996 | Legg et al. |
| 5,515,853 A | 5/1996 | Smith et al. |
| 5,524,620 A | 6/1996 | Rosenschein |
| 5,544,654 A | 8/1996 | Murphy et al. |
| 5,562,095 A | 10/1996 | Downey |
| 5,592,942 A | 1/1997 | Webler et al. |
| 5,596,653 A | 1/1997 | Kurokawa |
| 5,596,990 A | 1/1997 | Yock et al. |
| 5,618,266 A | 4/1997 | Liprie |
| 5,626,829 A | 5/1997 | Koutrouvelis |
| 5,643,171 A | 7/1997 | Bradshaw et al. |
| 5,647,663 A | 7/1997 | Holmes |
| 5,651,043 A | 7/1997 | Tsuyuki et al. |
| 5,651,364 A | 7/1997 | Yock |
| 5,660,180 A | 8/1997 | Malinowski et al. |
| 5,676,151 A | 10/1997 | Yock |
| 5,682,897 A | 11/1997 | Pomeranz |
| 5,683,345 A | 11/1997 | Waksman et al. |
| 5,701,900 A | 12/1997 | Shehada |
| 5,707,332 A | 1/1998 | Weinberger |
| 5,740,225 A | 4/1998 | Nabatame |
| 5,810,007 A | 9/1998 | Holupka |
| 5,842,473 A | 12/1998 | Fenster |
| 5,844,241 A | 12/1998 | Liu et al. |
| 5,859,891 A | 1/1999 | Hibbard |
| 5,868,673 A | 2/1999 | Vesely |
| 5,870,697 A | 2/1999 | Chandler et al. |
| 5,882,291 A | 3/1999 | Bradshaw et al. |
| 5,897,495 A | 4/1999 | Aida et al. |
| 5,919,135 A | 7/1999 | Lemelson |
| 6,032,678 A | 3/2000 | Rottem |
| 6,038,283 A | 3/2000 | Carol et al. |
| 6,049,729 A | 4/2000 | Cook et al. |
| 6,058,323 A | 5/2000 | Lemelson |
| 6,083,167 A | 7/2000 | Fox et al. |
| 6,095,975 A | 8/2000 | Silvern |
| 6,129,670 A | 10/2000 | Burdette et al. |
| 6,167,296 A | 12/2000 | Shahidi |
| 6,360,116 B1 * | 3/2002 | Jackson, Jr. et al. ........ 600/427 |

OTHER PUBLICATIONS

Pini, Riccardo, et al., "Echocardiographic Three–Dimensional Visualization of the Heart"; NATO ASI Series, vol. F60, 3D Imaging in Medice, pp. 263–274, 1990.

Nath, et al, "Dosimetry of Interstitial Brachytherapy Sources: Recommendations of the AAPM Radiation Therapy Task Group No. 43", Med. Phys., 22 (2): 209–234 (Feb. 1995): new trailer Novoste™ 1996 Annual Report.

"Hyal Receives First U.S. Patent Allowance for Prevention of Restenosis", Canada News Wire, Dec. 1996.

Fox, et al, "Calculated Dose Distribution of Beta–Particle Sources Used for Intravascular Brachytherapy", International Journal of Radiation Oncology Biology–Physics (America Society of Therapeutic Radiology and Oncology—ASTRO); vol. 39, No. 2, Supplement 1997, pp. 344.

Moran, F. "Management of Restenosis: The Callenge for Angioplasty in the 1990's", Midwest Cardiovascular Institute, Good Samaritan Hospital, Viewpoint, Winter 1996.

Mintz, Gary S. et al. "Intravascular Ultrasound Predictors of Restenosis after Percutaneous Transcatheter Coronary Revascularization", J. Am., Coll. Cardiol., 27:1678–1687, 1996.

Soares, et al., "Calibration and Characterization of BetaParticle Sources for Intravascular Brachytherapy", Med. Phys., 25(3):339–346, 1998.

EndoSonics, "Oracle® Imagining System IntraCoronary Ultrasound Imaging", pp. 1–3 (Website date Dec. 10, 1997).

EndoSonics, In–Vision™ The Future In IntraCoronary Ultrasound Now . . . pp. 1–6 (Website date Dec. 10, 1997).

Zamorano, Lucia, et al, "Image–Guided Stereotactic Centered Craniotomy and Laser Resectionof Solid Intracranial Lesions", Proceedings of the Xth Meeting of the World Society for Stereotactic and Functional Neurosurgery, Maebashi, Japan, Oct. 1989, Stereotact Funct Neurosurg, 1990; 54+55, pps. 398–403.

Peters, et al, "Integration of Sterescopic DSA with Three–Dimensional Image Reconstruction for Stereotactic Planning", Proceedings of the Xth Meeting of the World Society for Stereotactic and Functional Neurosurgery, Maebashi, Japan, Oct. 1989, Stereotact Funct Neurosurg, 1990; 54+55, pps. 471–476.

MMS—B3DTUI, Multimedia Medical Systems, dated rpior to Feb. 6, 1998.

Therepac Plus, Pinecliff Associates, dated prior to Feb. 6, 1998.

Hermiller, James B. MD, et al, "Quantitative and Qualitative Coronary Angiographic Analysis: Review of Methods, Utility, and Limitations", Catheterization and Cardiovascular Diagnosis, 1992, 25, pps. 110–131.

* cited by examiner

BRACHYTHERAPY SYSTEM FOR PROSTATE CANCER TREATMENT WITH COMPUTER IMPLEMENTED SYSTEMS AND PROCESSES TO FACILITATE PRE-IMPLANTATION PLANNING AND POST-IMPLANTATION EVALUATIONS WITH STORAGE OF MULTIPLE PLAN VARIATIONS FOR A SINGLE PATIENT

PRIORITY

This application claims the benefit of U.S. Provisional Application No. 60/076,226, filed Feb. 27, 1998.

FIELD OF THE INVENTION

The invention relates to computer implemented systems and processes to facilitate pre-implantation planning and post-implantation evaluations of image-guided brachytherapy procedures for treatment of prostate cancer.

BACKGROUND OF THE INVENTION

Brachytherapy procedures for treatment of prostate cancer are well known. Brachytherapy involves treating cancer by precisely locating a plurality of radiation sources (e.g., pellets of a radioactive isotope or "seeds") inside a human body in a three-dimensional array. Small amounts of a radioactive isotope, such as iodine-125 or palladium-103, are encapsulated in a suitable casing to form the seeds which are implanted. The seeds are placed in the treatment area according to a seed placement plan.

At least four major steps are performed in a brachytherapy procedure for the treatment of prostate cancer using a perineal approach to the prostate guided by, for example, transrectal ultrasonography. First, a transrectal ultrasound study or other suitable imaging technique is used to gain information concerning the location, size and positioning of a patient's prostate, surrounding tissues and surrounding organs. The imaging of the structures may be in the form of a visual image on a suitable medium or in the form of electronic data. In the former case the image may be captured as, for example, an ultrasound film or ultrasound Poloroid® scan which is then digitized by manually outlining the desired features. In the latter case, for example, raw ultrasound data may be captured and stored in electronic format. Ultrasound data may also be in the form of a VCR tape of an ultrasound study.

Second, a pre-implantation seed placement plan is developed to determine the desired location of the seeds in a three-dimensional space. A goal of the seed placement plan is to enable sufficient doses of radiation to impinge on the target structures or portions of structures needing treatment, while minimizing radiation to other structures or portions of structures in and near the treatment area, such as healthy tissue of the adjacent rectum and bladder. General criteria for establishing seed placement plans is known. In general, the process of generating a seed placement plan involves proposing the location of a plurality of seeds in a three-dimensional space, and, based on the known radiation characteristics of the seeds, calculating the radiation dose levels within the treatment area resulting from the proposed seed placement. The effectiveness of the proposed plan may conveniently be determined through the use of isodose lines which may be displayed for the user. Various revisions to the plan and reevaluation may be made in an attempt to optimize the plan. Each iteration of revisions to the plan and reevaluation is time consuming since it requires recalculation of the dosimetry and the expected results for each proposed placement plan.

Once an acceptable plan is developed, the third step is to physically implant the seeds according to the optimized seed placement plan and using known brachytherapy protocols. The seeds are typically delivered and positioned using needles which are inserted through a catheter or microcatheter. One method of increasing the accuracy of placement involves placing a needle guide template over the perineum to assist the physician in placing the seeds in the patient's prostate. The needle guide template is a physical device of known geometry containing holes with predetermined (e.g., half-centimeter) spacing. The needle guide template may be registered by identifying two known landmarks in a captured image and accounting for any relative translation, rotation, or scaling of the image.

The last major step in the procedure may include a post-implant evaluation procedure. In this step, the actual location of the seeds is determined and compared with the intended seed location as specified in the seed placement plan. To do this, post-implementation images of the treatment area are taken, so that the actual location of each seed can be identified. Imaging techniques which are distinct from those used for pre-implantation are typically used during the post-implantation phase. After obtaining the post-implantation imaging, a comparison of each seed's planned location with its actual location may be made. If necessary, further implantation may be performed or the previous implantation locations may be adjusted according to medically known procedures.

Computer implemented systems for assisting with some or all of the above steps are known. Software for one such system is available from Multimedia Medical Systems, the assignee of the present invention, and others. One such system is marketed by the assignee as MMS Therpac-PLUS™ Version 6.5. These known systems are useful in assisting with certain aspects of the pre-implantation plan and the post-implantation evaluation, but have various limitations and drawbacks.

While known systems are generally effective in developing and implementing a seed placement plan according to the specific aspects of each patient's physiological makeup, they are often deficient when it is necessary or desirable to develop multiple, alternative seed placement plans and work with them over time until the most beneficial plan is selected for implementation. This is especially true in connection with complex placement plans that require multiple iterations to optimize. In particular, known systems do not typically permit user-friendly and efficient evaluation, storage and selection between and among multiple seed placement plans.

SUMMARY OF THE INVENTION

An object of the invention is to overcome the limitations and drawbacks of prior systems.

Another object of the invention is to provide a computer implemented system and process for facilitating seed placement planning and post-implantation evaluations wherein multiple variations of such plans and evaluations are easily accessible and may be compared against one another.

Another object of the invention is to permit access to and manipulation of seed placement plans and post-implantation evaluations in a user-friendly and efficient manner.

According to one aspect of the invention, multiple variations of pre-implantation seed placement plans and post-implantation evaluations may be simultaneously created, stored, retrieved and manipulated. Each variation may contain one or more distinctions from other variations. The variations are stored in the system and may be compared against one another in order to systematically select the most beneficial plan or determine the most likely effect of implantation following the implantation procedure.

These and other objects, aspects, and features of the present invention shall become apparent from the accompanying figures and the detailed description thereof.

DETAILED DESCRIPTION OF THE EMBODIMENTS OF THE INVENTION

In order to illustrate the multiple variations of plans available for comparison and selection in connection with the pre-implantation and post-implantation steps, it is useful to briefly describe the pre-implantation planing steps and the post-implantation steps.

Figure 1:
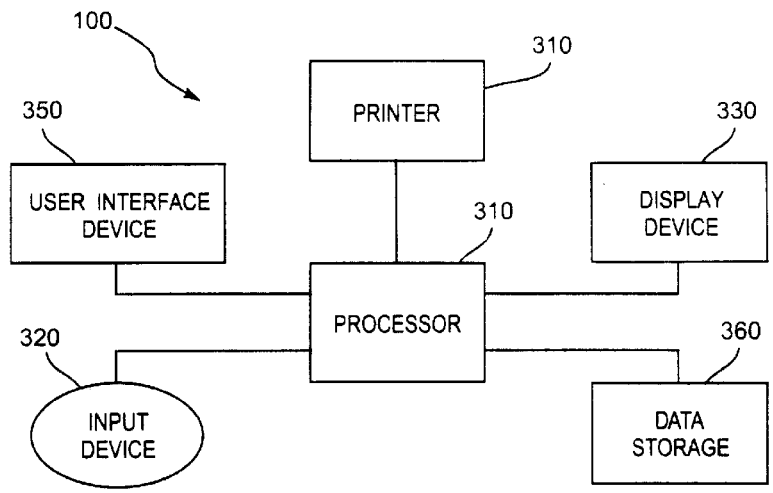
FIG. 1 is a block diagram of the brachytherapy pre-implantation planning and post-implantation evaluating system.

FIG. 1 is a schematic block diagram depicting an example of a brachytherapy pre-implantation planning and post-implantation evaluating system 100 according to one embodiment the present invention. As shown, system 100 may comprise a processor 310, an input device 320, user interface device 350, a display device 330, data storage device 360 and a printer 340. Processor 310 may be a personal computer running an operating system such as Microsoft Windows 95 or Microsoft Windows NT. Some or all of the steps associated with the present invention may be implemented through application software resident on system 100. Input device 320 loads image scans from an imaging device, such as an ultrasound or computerized tomography (CT) scan device, into system 100 such that the image is stored electronically in data storage 360. Input device 320 may be, for example, an optical scanner. In a preferred embodiment of the invention, input device 320 comprises a digitizer from the AccuGrid line of digitizer tablets available from the Numonics Corporation or another similar digitizer. Images may be catalogued, stored and retrieved using an appropriate document management system or through operating system software.

A user of system 100 may view the image scans on display device 330 once they are loaded into system 100. Additionally the user may employ system 100 to manipulate the image scans as desired through commands entered at user interface device 350 which may be a keyboard, mouse, joystick, touchscreen, any combination of the above or other suitable input device. The user may print out image scans and other data resident on system 100 using printer 340.

Figure 2:
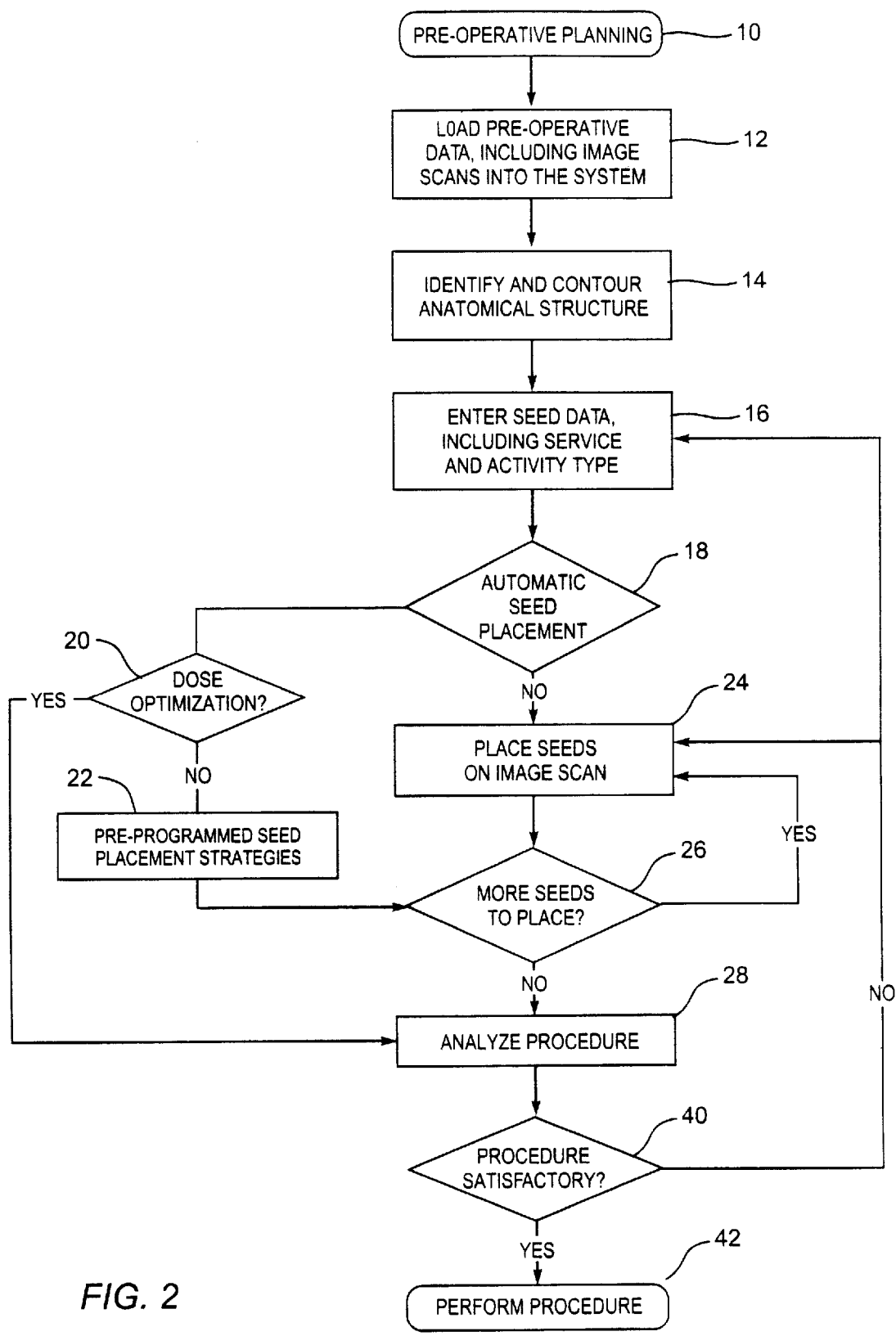
FIG. 2 is a flow chart of the pre-implantation planning of one embodiment of the invention.

System 100 directs a user through a series of steps in designing a pre-implantation brachytherapy plan, as illustrated by the flowchart of FIG. 2. Preferably, the user is stepped through the process via a graphical user interface generated by processor 310 and displayed on display device 330. The user enters commands and controls the process through the use of user interface device 350. System 100 begins at step 10 in performing a pre-implantation plan and loads pre-implantation data at step 12. During this step, the pre-implementation image scans associated with the selected patient are loaded. The image scans may be acquired through various techniques. For example, some techniques may include direct video capture from an ultrasound device or a video tape of the procedure, transmission and acquisition using DICOM (Digital Imaging and Communications in Medicine) standard data, or magnetic digitization (e.g., using a backlit magnetic digitizer tablet, similar to digitizer tablets used for CAD/CAM applications).

In addition to imaging data, pre-implantation data may also include the identity of and other characteristics of the patient (e.g., social security number, date of birth. etc.), the identity of an initial user first creating or accessing a file, and the type of study to be conducted (e.g., a pre-implantation ultrasound video acquisition study, a pre-implantation ultrasound digitization study, a pre-implantation ultrasound file import study or other types of studies). Pre-implementation data may be entered by the user either directly (e.g., through a keyboard) or via pull down menus or other selection mechanism.

In step 12, the actual patient imaging data is loaded into system 100. There are various methods for accomplishing this. One method is to directly connect processor 310 or input device 320 to an ultrasound device or other imaging apparatus. In this case, raw ultrasound data is captured in real time as the ultrasound procedure is taking place. Other methods include entering ultrasound films or ultrasound scans into a digitizer connected to processor 310 or input device 320, or loading image computer files into system 100 through a disk drive or network. Other methods of loading images may also be used.

Figure 3:
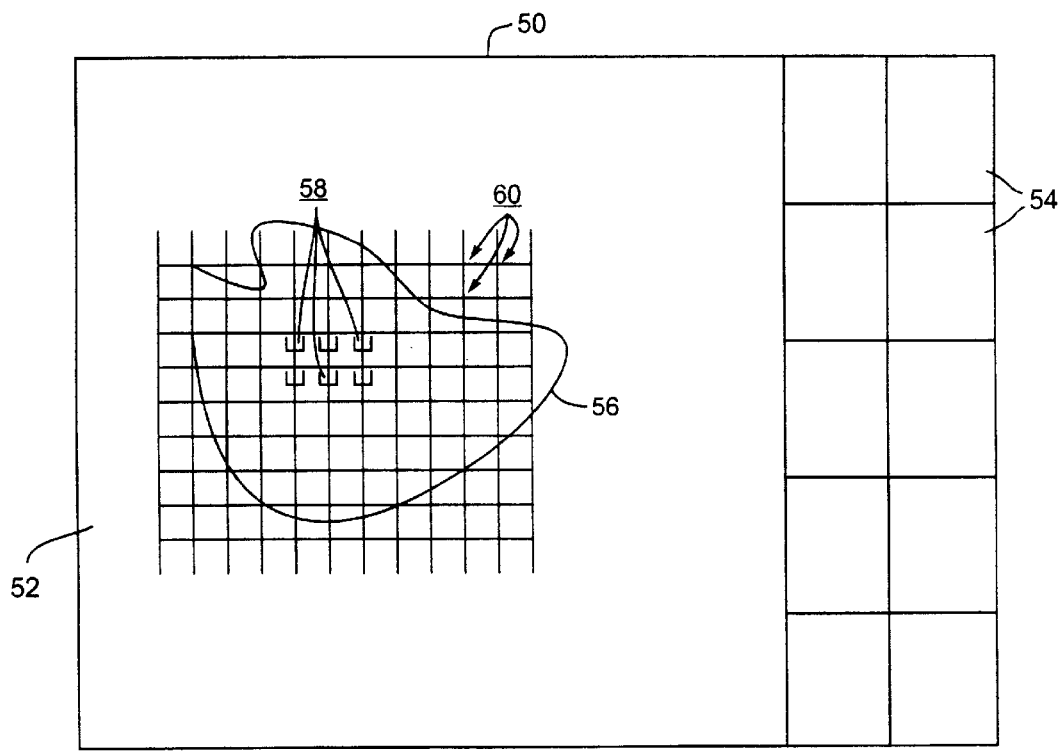
FIG. 3 is an example of a graphical user interface that illustrates various aspects of seed placement or identification in one embodiment of the invention.

After the desired image or images have been loaded into system 100, a system window 50 (as illustrated in FIG. 3) which may be provided on display device 330 displays one relatively large image scan in a working window 52, and a plurality of other relatively smaller images in thumbnail windows 54. This layout allows the user to view multiple image scans while designing a pre-implantation plan. In this embodiment it is possible to store, manipulate, locate and compare different seed placement plans as discussed in further detail below. For example, working window 52 may display a placement plan immediately under consideration while allowing, easy reference to other variations previously considered or to be considered via a variation selection menu.

At step 14, system 100 prompts the user to select a computer generated template and position it over image scans as displayed on display device 330 in order to identify predetermined structures. It is necessary to complete template registration before it is possible to outline structures or place seeds. Template registration ensures that captured images are properly aligned with the template. Once the template has been registered, the user may identify and contour anatomical structures through user interface device 350, the aforementioned templates and other available tools which function to contour an/or outline various anatomical structures. The relevant structures in brachytherapy treatment may include (but are not limited to) the prostate, rectum, urethra, and bladder. System 100 supports several standard templates for preoperative planning. FIG. 3 illustrates an anatomical structure 56 as outlined using user interface device 350 of system 100. The structure appears as the light, somewhat circular outline in FIG. 3.

After the anatomical structures which may impact treatment have been located and outlined at step 14, system 100 prompts the user to enter seed data at step 16. Seed data may include information about the seed, such as the type of radioactive material used for a seed, and the activity of the seed material. Other seed data may also be entered.

System 100 preferably allows the user to opt for either automatic seed placement or manual seed placement in response to a query by system 100 at step 18. If manual placement is selected, processing continues at step 24, which will be described later. If automatic seed placement is selected, the system 100 allows a user to choose whether to use dose optimization at step 20 or not. If dose optimization is selected at step 20, system 100 places seeds according to various user defined criteria. These criteria may include specifying a particular dose applicable to a particular anatomical structure or structures, such as the cancer to be treated, or the neighboring anatomical structures. If a user selects dose optimization, the criteria are converted to an error function and an optimal plan is generated through a simulated annealing procedure. If a user elects not to select dose optimization at step 20, system 100 may place seeds in pre-programmed seed placement strategies at step 22. Such pre-programmed placement strategies correspond to known brachytherapy methods that create either a uniform or peripherally-weighted placement pattern. After a pre-programmed seed placement strategy has been performed, a user may then decide to modify the treatment at step 26 to alter the plan and selectively add, delete, move, or otherwise alter seed locations and parameters.

System 100 allows the user to alternatively manually specify seed placement on image scans at step 24. FIG. 3 illustrates one embodiment of how an image scan might appear to a user while the user is manually specifying seed locations. Seeds 58 may be located by the user on intersecting grid lines forming nodes 60 as displayed in window 52 so as to specify seed placement according to a pre-implementation plan. After the user has designated the placement of a seed 58 on an image scan, a user may continue to place seeds by going back to step 24 until all seeds are located. Once the target dose value has been designated in step 16 and at least one seed has been placed in step 24, the DVH/CVA (Cumulative Dose Histogram/Contiguous Volume Analysis) plots become available for view (assuming at least one anatomical structure has been outlined).

As seeds are placed, system 100 preferably initiates an Analysis Procedure at step 28 to analyze the pre-implantation plan. According to this Analysis Procedure, the user, using user interface device 350, may vary particular aspects of the seed placement plan with system 100 providing a real-time response to the user's changes. For example, system 100 preferably displays isodose lines which illustrate the effect of the proposed treatment plan as the user modifies the plan. These isodose lines are displayed in working window 52 and thumbnail windows 54. System 100 preferably allows the user to adjust various aspects of the seed placement plan including the target dose value, seed positions and needle paths.

System 100 may also update information sections of the contained in window 50. These information sections may include the total number of seeds designated on a particular image scan, the total number of seeds designated on all of the image scans or any other information relating to the seed placement plan. The user may view a treatment program in a two-dimensional view by designating a specific section slice to be displayed, or, alternatively, system 100 allows the user to view a treatment program in a three-dimensional view.

The user may also view a plan through DVH and CVA plots. A DVH displays a plot of the structure volume that receives a particular dose, e.g., what percentage of the volume of the structure receives a given dose of radiation. A CVA displays a plot of the homogeneity of a radiation dose rate for a target volume, e.g., what actual volume (either total or contiguous) receives a given does of radiation.

After analyzing a pre-implantation plan, the user is prompted to decide at step 40 whether the devised plan is appropriate for a patient. If the plan is not satisfactory, the user may, for example, decide to alter seed locations at step 24, or decide to alter seed data at step 16 to reflect alternative seed characteristics. Other options may also be available to the user. Once a pre-implantation plan is selected, the treatment plan can be implemented at step 42. Implementation of a selected plan may comprise qualified medical personnel implanting the seeds using conventional means, such as a transperineal implantation technique.

Pre-implantation planning may also be performed in a real-time environment. Planning and evaluation may occur as the implantation is occurring. Thus, during an implantation procedure, the user may view information on display device 330. From this information, the user may then determine whether the current seed implantation is correct and where to place the next seed.

Post-Implantation Evaluations

Figure 4:
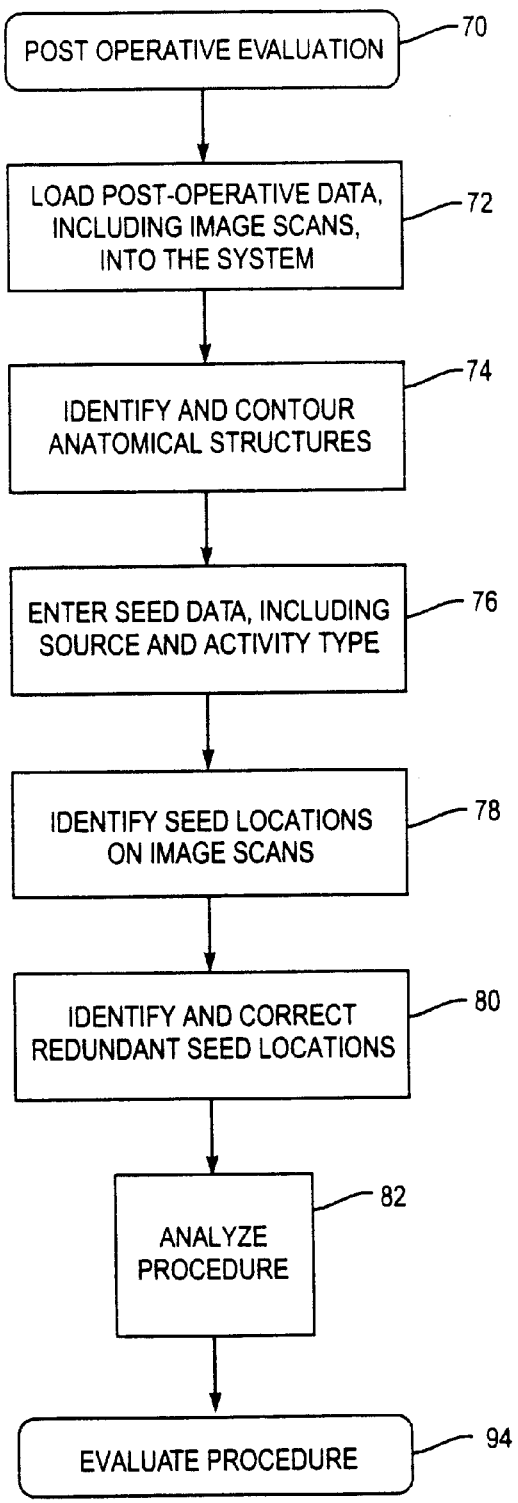
FIG. 4 is a flow chart of the post-implantation evaluation process of one embodiment of the present invention.

System 100 also provides a post-implantation evaluation option, as illustrated by the flowchart in FIG. 4. The purpose of the post-implantation evaluation is to allow a user to evaluate the effectiveness of the seed placement procedure by pre-computing radiation dosage levels based on actual seed placement obtained in the seed implantation procedure. Post-implantation evaluation does differ from pre-implantation seed placement in some aspects. For example, image data from post-operative evaluations typically comes from CT films or stereo-shift films rather than from ultrasound images. Also, redundancy correction techniques are typically used during post-implantation evaluation to eliminate false (duplicate) seeds from consideration. In addition, templates are not used during post-implantation evaluation.

Figure 5:
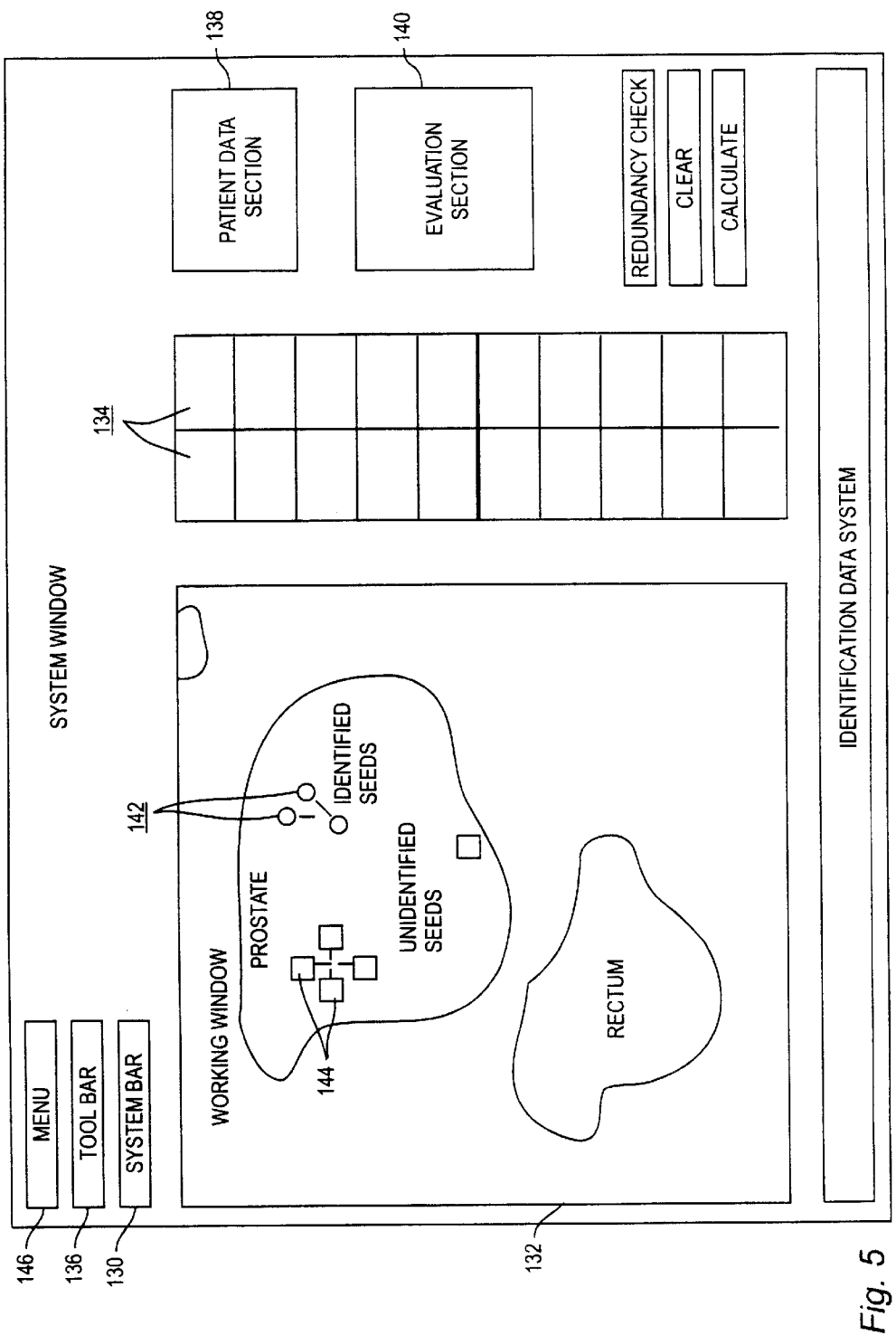
FIG. 5 is an example of a graphical user interface that illustrates various aspects of seed identification in a post-implantation evaluation.

FIG. 5 is an exemplary display screen which may represent the graphical user interface presented to the user on display device 330 during post-implantation evaluation. The display in FIG. 5 provides a presentation depicting the location of seeds on an image scan according to one embodiment of the present invention. This image scan represents actual imaging data taken from a patient following an actual implantation procedure.

System 100 presents the user with a system window 130, which includes a central working window 132 and thumbnail windows 134, which may be presented, for example, in two columns. Working window 132 includes a detailed image of a selected view while thumbnail window 134 includes other images loaded into the system. A tool bar 136 portion along the top of the display screen allows a user to manipulate data, images and system characteristics in a well known manner.

For example, pull down menus on menu bar 146 allow a user to manipulate the system configuration through user interface device 350. In FIG. 5, menu bar 146 contains pull down menus entitled "File," "View," "Variations," "Configurations," and "Help." The "File" menu allows a user to open and close various studies, as well as print the currently selected study. The "View" menu presents a user with the options to manipulate the view seen by the user, such as altering the shading, or enlarging or reducing the size of an image. The user may also interact with system 100 to select how many image scans are displayed in thumbnail window 134. With the "Variations" pull-down menu, a user may create new variations of a plan or evaluation, rename a current variation, or delete a variation. Variations (including their purpose, use and operation) are discussed in detail below. The "Configuration" menu allows the user to manipulate the configuration and operation of system 100. The "Help" menu may provide information about system 100, as well as assisting the user in operating system 100.

As illustrated in FIG. 5, a toolbar 136 is located below the menu bar 146 on the system window 130. The tool bar 136 contains buttons which perform a variety of functions, such as saving the current version of the study, printing the current copy of the reports, enlarging an image scan, changing the canvas layout, or other controls. Other options may also be available in the menu bar 146 and toolbar 136.

Patient data section 138 of system window 130 may display information about a patient and a particular procedure being evaluated. This information may include the name of patient, medical history, including the treatment plan, proposed seed placement plan, the date the implantation procedure was performed, and similar information. A system window 130 may also present a user with an evaluation section 140, which presents summary information about the graphic display, such as target dose and isodose mapping information. The user may evaluate an image scan or image scans by viewing isodose lines.

If the user desires to perform a post-implantation evaluation according to an embodiment of the invention, system 100 will enter the implantation evaluation at step 70 and load post-implantation data at step 72. Post-implantation data may include the patient's medical history file and raw imaging data, such as image scans, in a manner similar to creating a pre-implantation plan. At step 74, the user identifies and contours anatomical structures in image scans in a manner similar to pre-implantation planning, so as to outline and identify major structures and organs. At step 76, the user enters seed data, such as the radioactive composition of the seed and the activity level of a given seed. At step 78, the user is prompted to identify seeds that are visible in the image scan on display device 330 by designating a portion of an image scan using user interface device 350. This procedure is similar to placing seeds in the pre-implantation planning, except that seeds are identified in accordance with their actual location in the image scan. As the user identifies the locations of various seeds, system 100 may provide an identification number for each seed. An identification number may, for example, be given in the order the seeds are located and identified to the system (e.g., the twelfth seed located is identified as seed #12. etc.). The identification numbers may be used to later identify the seeds for evaluation or in connection with the elimination of redundant (false) seeds.

A detailed graphical presentation of the target area and surrounding tissue is displayed in working window 132 using false coloring or a gray level scale to represent tissue density or other characteristics provided by conventional medical imaging apparatus and systems, such as ultrasound, CT, MRI, etc. At step 80, system 100 attempts to isolate and identify structures having characteristics known to correspond to the seeds, such as high density, high reflectivity, etc. System 100 then indicates that a structure has been tentatively identified as a seed by displaying an identification icon corresponding to the location of all such structures. The icon may be, for example, a small circle positioned in the middle of the area tentatively identified as containing a seed.

According to an embodiment of the invention, a user may be prompted to initiate an automatic seed identification ("ASI") process. System 100 preferably automatically identifies the location of seeds based on image scans. The ASI process may obviate the step of identifying and correcting redundant seed locations.

The user is presented with a number of unidentified seeds 144 shown on image scans. In one embodiment, working window 132 display's an image scan with unidentified seeds 144. A user may then locate the seeds on an image scan in working window 132, as shown by identified seeds 142. The user may identify resolve, and correct redundant seed locations. Once this is accomplished, the user may view the procedure results according to the Analyze Procedure step (step 82) through a variety of different methods. In one method, the user may manipulate isodose lines in a similar manner to a pre-implantation procedure. Also, a user may view a plan in a two-dimensional view, while another option allows a user to view a plan in a three-dimensional view. Similarly, the user may view the results through DVH and/or CVA plots. The DVH plots and CVA plots are similar to those viewed in the pre-implantation planning.

Multiple Variations

According to one particular aspect of the invention, the user may create multiple variations of pre-implantation plans and/or post-implantation evaluations. Using multiple variations, the user may work with a number of pre-implantation plans and/or post-implantation evaluations and individually store each plan for later retrieval and review. In this manner, for example, a user could create several versions of a pre-operative plan, each with a different number of seeds, different seed placement method, different seed activity level and even different isotopes. The target dose and isodose contours may also be varied among different versions. In the post-implantation evaluation mode and as another example, the user could perform one redundancy correction where redundant seeds are deleted, and another redundancy correction where redundant seeds are merged. The stored evaluations in this case could later be compared to select the best fit.

In a preferred embodiment, when certain specified parameters in a default version or in a variation are changed, the change is propagated to all other variations in that study. For example, a change in what colors are assigned to associated attributes might be propagated. Additionally, an addition or deletion of a structure outline from a scan to one variation might be applied to all other variations automatically. In contrast, other parameters might be identified as variation specific. For example, each of the following parameters might be selected as variation specific:

Target Dose; Isotope; Activity Level; Seed Positioning; Anisotropy Correction Status; and Isodose Levels.

The particular parameters which are variation specific versus those that should be propagated may be set by the user using, for example, a pull down menu, or, alternatively, this configuration may be provided at install time or by a system administrator.

Figure 6:
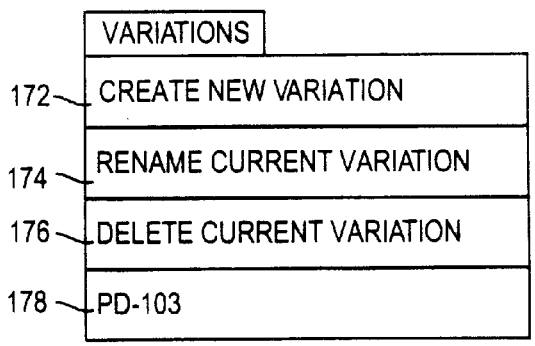
FIG. 6 is an example of a graphical user interface which illustrates a pull-down menu presented to a user to operate variations of a post-implantation evaluation.

A pull-down menu 170 for working with variations may be presented to the user, as illustrated by way of example in FIG. 6. A user may create a new variation 172, rename a variation 174, or delete a variation 176. Pull-down menu 170 may also identify the variation 178 currently being used and/or others which have recently been accessed.

Figure 7:
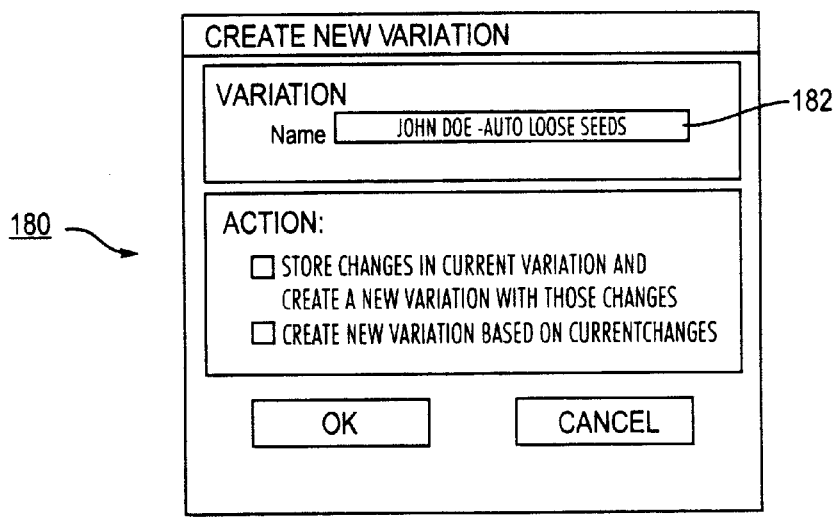
FIG. 7 is an example of a graphical user interface which illustrates a dialog box presented to a user to create variations of a post-implantation evaluation.

When creating a new variation, a user is presented with a new variation dialog box 180, as illustrated in FIG. 7. The name 182 of the new variation to be created may be entered using user interface device 356 (i.e., keyboard to enter data; mouse to select menu items), and in one embodiment of the invention, various options regarding a new variation may be presented to the user. For example, the user may save a variation in its current state while creating a new variation, based on the current state of the previous variation. The new variation diverges from the previous variation once the user begins to make changes to the new variation.

Figure 8:
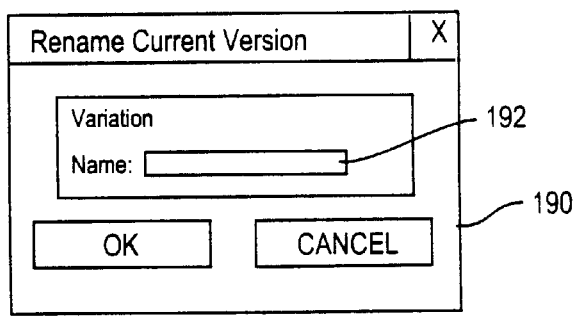
FIG. 8 is an example of a graphical user interface which illustrates a dialog box presented to a user to rename variations of a post-implantation evaluation.

A user may also change the name of a variation. As shown in FIG. 8, a rename variation dialog box 190 is presented to a user. A user enters a new name 192 for the variation, and activates the rename variation function, thereby excepting the new name. A user may also delete a variation be activating the delete variation function 176 (FIG. 6).

The system of the present invention allows a user to move easily between a number of variations of pre-implantation plans or post-implantation evaluations. Thus, for example, a user could create an original pre-implantation plan using specific values and placements for various seed. The user could then create a variation on the original pre-implantation plan and vary either the seed values, or the seed positions, or both and then compare the variations. This comparison allows the user to determine which plan better meets the treatment goals and objectives for the patient. If desired, the user may create more pre-implantation variations (as many as desired up to the resource limits of system 100), varying different parameters and then comparing the different variations.

In a preferred embodiment of the present invention, system 100 allows a user, when creating a new variation, to choose which state to leave current variation in when system 100 creates a new variation. The user may either (i) store the changes in the current variation and create a new variation with those changes or (ii) create a new variation based upon the current changes to the current variation. According to a preferred embodiment, the state of the new variation is the same with either choice. The difference is in the state of the previously current variation. If the first option is selected, system 100 saves the current version in its current state and creates a new variation. At that moment, the two variations are identical. They diverge when changes are made to the new variation. If the second option is selected, system 100 creates a new version as it exists at that moment and leaves the previously current version in its state when it was last saved. Any changes to the previously current version since it was last saved are not saved with respect to the previously current version. This option therefore allows the user to decide after one or more variation specific changes have been made that they should be stored in the new variation but not in the previously current variation.

Variations may be renamed, deleted and added as desired by the user. When a variation is deleted, the first (default) variation preferably replaces the deleted variation in window 52 or window 132 as appropriate.

Although the invention has been described in the context of treating prostate cancer in humans, it is equally applicable to treatment plans and implementations in a wide range of human and animal procedures and to other imaging systems used to plan, assist, monitor and confirm the placement of objects within a body. These and other embodiments and uses of the invention will be apparent to those skilled in the art from consideration of the specification and practice of the invention disclosed herein. The specification and examples should be considered exemplary only. The scope of the invention is only limited by the claims appended hereto.

What is claimed is:

1. In a computer implemented system for assisting in an interstitial radiation therapy treatment, where the computer receives two-dimensional images of a three-dimensional treatment area and the computer system comprises a display for graphically displaying the two-dimensional images, and a processor for creating interstitial radiation therapy treatment plans, a method comprising the steps of:

providing variation specific parameters;

creating an earlier plan using variation specific parameters;

creating a variation plan by manipulating variation specific parameters of the earlier plan; and displaying the earlier plan and the variation plan on the display, wherein the earlier plan and the variation plan are mutually accessible for comparison on the display.

2. The method according to claim 1, wherein the step of creating the variation plan further comprises:

(a) saving the earlier plan;

(b) manipulating variation specific parameters of the earlier plan; and (c) creating a variation plan; and the step of displaying further comprises displaying the saved earlier plan and the variation plan.

3. The method according to claim 2, wherein variation specific parameters comprise at least one of:

a. a target dosage;

b. a radiation source type;

c. a radiation source activity level;

d. radiation source positioning;

e. an anisotropy correction constant;

f. a list of isodose values for two-dimensional display; and g. an isodose level of three-dimensional display.

4. The method according to claim 1, wherein the step of creating the variation plan further comprises:

(a) saving the earlier plan;

(b) creating a variation plan, where the variation plan in identical to the earlier plan; and (c) manipulating variation specific parameters of the variation plan; and the step of displaying further comprises displaying the saved earlier plan and the manipulated variation plan.

5. The method according to claim 4, wherein variation specific parameters comprises at least one of:

a. a target dosage;

b. a radiation source type;

c. a radiation source activity level;

d. radiation source positioning;

e. an anisotropy correction contact;

f. a list of isodose values for two-dimensional; and g. an isodose level for three-dimensional display.

6. The method according to claim 1, further comprising the steps of: saving at least one of the earlier plan and the variation plan.

7. The method according to claim 1, further comprising the step of:

recalling a saved plan, wherein the saved plan is one of a saved earlier plan and a saved variation plan; and comparing the saved plan to the other of the variation plan or the earlier plan.

8. The method according to claim 1, further comprising the step of designating the variation specific parameters.

9. In a computer implemented system for assisting in an interstitial radiation therapy treatment, where the computer receives two-dimensional images of a three-dimensional treatment area and the computer system comprises a display for graphically displaying the two-dimensional images, and a processor for creating interstitial radiation therapy treatment evaluations of the treatment area, a method comprising steps of:

providing variation specific parameters;

creating an earlier evaluation using variation specific parameters;

creating a variation evaluation by manipulating variation specific parameters of the earlier evaluation; and displaying the earlier evaluation and the variation evaluation on the display, wherein the earlier evaluation and the variation evaluation are mutually accessible for comparison on the display.

10. The method according to claim 9, wherein the step of creating the variation evaluation further comprises:

(a) saving the earlier evaluation (b) manipulating variation specific parameters of the earlier evaluation; and (c) creating a variation evaluation; and the step of displaying further comprises displaying the saved earlier evaluation and the variation plan.

11. The method according to claim 10, wherein variation specific parameters comprise at least one of:

a. a target dosage;
b. a radiation source type;
c. a radiation source activity level;
d. radiation source positioning;
e. an anisotropy correction constant;
f. a list of isodose values for two-dimensional display; and
g. an isodose level for three-dimensional display.

12. The method according to claim 9, wherein the step of creating the variation evaluation further comprises:

(a) saving the earlier evaluation;

(b) creating a variation evaluation, where the variation evaluation is identical to the earlier evaluation; and (c) manipulating variation specific parameters of the variation evaluation; and the step of displaying further comprises displaying the saved earlier evaluation and the manipulated variation evaluation.

13. The method according to claim 12, wherein variation specific parameters comprise at least one of:

a. a target dosage;
b. a radiation source type;
c. a radiation source activity level;
d. radiation source positioning;
e. an anisotropy correction constant;
f. a list of isodose values for two-dimensional display; and
g. an isodose level for three-dimensional display.

14. The method according to claim 10, further comprising the steps of:

saving at least one of the earlier evaluation and the variation evaluation.

15. The method according to claim 10, further comprising the steps of:

recalling a saved evaluation, wherein the saved evaluation is one of a saved earlier evaluation and a saved variation evaluation; and comparing the saved evaluation the other of the variation evaluation or the earlier evaluation.

16. The method according to claim 9, further comprising the steps of designating the variation specific parameters.

17. A computer implemented system for assisting in an interstitial radiation therapy treatment, the system comprising:

means for receiving a plurality of two-dimensional images of a three-dimensional treatment area;

means for providing variation specific parameters;

means for creating an earlier interstitial radiation therapy treatment plan in the treatment area using variation specific parameters; and means for creating a variation plan, wherein the earlier plan and the variation plan are mutually accessible for comparison on the display means.

18. The system according to claim 17, wherein creating the variation plan further comprises:

(a) saving the earlier plan;

(b) manipulating variation specific parameters of the earlier plan; and (c) creating a variation plan; and displaying further comprises displaying the saved earlier plan and the variation plan.

19. The system according to the claim 18, wherein variation specific parameters comprise at least one of:

a. a target dosage;
b. a radiation source type;
c. a radiation source activity level;
d. radiation source positioning;
e. an anisotropy correction constant;
f. a list of isodose values for two-dimensional display; and
g. an isodose level for three-dimensional display.

20. The system according to claim 17, wherein creating the variation plan further comprises:

(a) saving the earlier plan;

(b) creating a variation plan, where the variation plan is identical to the earlier plan; and (c) manipulating variation specific parameters of the earlier plan; and displaying further comprises displaying the saved earlier plan and the manipulated variation plan.

21. The system according to claim 20, wherein variation specific parameters comprise at least one of:

a. a target dosage;
b. a radiation source type;
c. a radiation source activity level;
d. radiation source positioning;
e. an anisotropy correction constant;
f. a list of isodose values for two-dimensional display; and
g. an isodose level for three-dimensional.

22. The system according to claim 20, further comprising:

means for saving at least one of the earlier plan and the variation plan.

23. The system according to claim 20, further comprising:

means for recalling a saved plan, wherein the saved plan is one of a saved earlier plan and a saved variation plan; and means for comparing the saved plan to the other of the variation plan or the earlier plan.

24. The method according to claim 20, further comprising the step of designating the variation specific parameters.

25. A computer implemented system for assisting in an interstitial radiation therapy treatment, the system comprising:

means for receiving a plurality of two-dimensional images of a three-dimensional treatment area;

means for providing variation specific parameters;

means for creating an earlier interstitial radiation therapy treatment evaluation in the treatment area using variation specific parameters;

means for creating a variation evaluation by manipulating variation specific parameters of the earlier evaluation; and means for displaying the earlier evaluation and the variation evaluation, wherein the earlier evaluation and the variation evaluation are mutually accessible for comparison on the display means.

26. The system according to claim 25, wherein creating the variation evaluation further comprises:

(a) saving the earlier evaluation;

(b) manipulating variation specific parameters of the earlier evaluation; and (c) creating a variation evaluation; and displaying further comprises displaying the saved earlier evaluation and the variation evaluation.

27. The system according to claim 26, wherein variation specific parameters comprise at least one of:

a. a target dose;

b. a radiation source type;

c. a radiation source activity level;

d. radiation source positioning;

e. an anisotropy correction constant;

f. a list of isodose values for two-dimensional display; and g. an isodose level for three-dimensional display.

28. The system according to claim 25, wherein the variation evaluation further comprises:

(a) saving the earlier evaluation;

(b) creating a variation evaluation, where the variation evaluation is identical to the earlier evaluation; and (c) manipulating variation specific parameters of the earlier evaluation; and displaying further comprises displaying the saved earlier evaluation and the manipulated variation evaluation.

29. The system according to claim 28, wherein variation specific parameters comprise at least one of:

a. a target dosage;

b. a radiation source type;

c. a radiation source activity level;

d. radiation source positioning;

e. an anisotropy correction constant;

f. a list of isodose values for two-dimensional display; and g. an isodose level for three-dimensional display.

30. The system according to claim 25, further comprising:

means for saving at least one of the earlier evaluation and the variation evaluation.

31. The system according to claim 25, further comprising:

means for recalling a saved evaluation, wherein the saved plan is one of a saved earlier evaluation and a saved variation evaluation; and means for comparing the saved evaluation to the other of the variation evaluation or the earlier evaluation.

32. The method according to claim 25, further comprising the step of designating the variation specific parameters.

* * * * *

UNITED STATES PATENT AND TRADEMARK OFFICE
CERTIFICATE OF CORRECTION

PATENT NO.      : 6,539,247 B2
DATED           : July 14, 2003
INVENTOR(S)     : Kevin Stewart Spetz It is certified that error appears in the above-identified patent and that said Letters Patent is hereby corrected as shown below:

Title page,
Item [56], References Cited, OTHER PUBLICATIONS, please replace "Imagining" with -- Imaging --.

Drawings,
Figure 1, please replace PRINTER reference numeral "310" with -- 340 --.

Column 10,
Line 47, immediately after the phrase "where the variation plan", please replace "in" with -- is --.

Column 12,
Lines 61 and 64, please replace "claim 20" with -- claim 17 --.

Column 13,
Line 3, please replace "claim 20" with -- claim 17 --.

Column 14,
Line 4, immediately after the word "wherein", please insert -- creating --.

Signed and Sealed this

Twenty-eighth Day of October, 2003

JAMES E. ROGAN
*Director of the United States Patent and Trademark Office*